(12) United States Patent
McHugo

(10) Patent No.: US 9,387,099 B2
(45) Date of Patent: Jul. 12, 2016

(54) NON-WOVEN HELICAL WIRE STENT

(75) Inventor: Vincent McHugo, County Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/564,148

(22) Filed: Aug. 1, 2012

(65) Prior Publication Data

US 2013/0197623 A1    Aug. 1, 2013

Related U.S. Application Data

(60) Provisional application No. 61/515,081, filed on Aug. 4, 2011.

(51) Int. Cl.
| | | |
|---|---|---|
| A61F 2/06 | (2013.01) |
| A61F 2/88 | (2006.01) |
| A61F 2/852 | (2013.01) |
| A61F 2/90 | (2013.01) |
| A61F 2/86 | (2013.01) |
| A61F 2/07 | (2013.01) |

(52) U.S. Cl.
CPC ............. *A61F 2/885* (2013.01); *A61F 2/852* (2013.01); *A61F 2/86* (2013.01); *A61F 2/90* (2013.01); *A61F 2/07* (2013.01); *A61F 2/88* (2013.01); *A61F 2210/0076* (2013.01); *A61F 2250/0018* (2013.01); *A61F 2250/0048* (2013.01); *A61F 2250/0063* (2013.01)

(58) Field of Classification Search
CPC .................................. A61F 2/852; A61F 2/885
USPC ............................. 623/1.22, 1.27, 1.32, 1.44
See application file for complete search history.

(56) References Cited

U.S. PATENT DOCUMENTS

| | | | | |
|---|---|---|---|---|
| 7,815,673 | B2 * | 10/2010 | Bloom et al. ................ | 623/1.15 |
| 8,114,147 | B2 * | 2/2012 | Wood et al. ................. | 623/1.15 |
| 2001/0044650 | A1 | 11/2001 | Simso et al. | |
| 2005/0256563 | A1 | 11/2005 | Clerc et al. | |
| 2009/0182407 | A1 * | 7/2009 | Leanna et al. .............. | 623/1.11 |
| 2009/0319017 | A1 | 12/2009 | Berez et al. | |
| 2011/0160836 | A1 | 6/2011 | Behan | |

OTHER PUBLICATIONS

Notification of Transmittal of the International Search Report and the Written Opinion of the International Searching Authority, or the Declaration, dated Oct. 31, 2012, for corresponding application PCT/US2012/049144, 4p.

* cited by examiner

*Primary Examiner* — Brian Dukert
(74) *Attorney, Agent, or Firm* — Brinks Gilson & Lione

(57) ABSTRACT

Exemplary non-woven helical stents are described that are efficient to fabricate in terms of labor and resources by being able to be manufactured by hand or machine while providing mechanical stability equivalent or close thereto of known braided or woven stents.

18 Claims, 6 Drawing Sheets

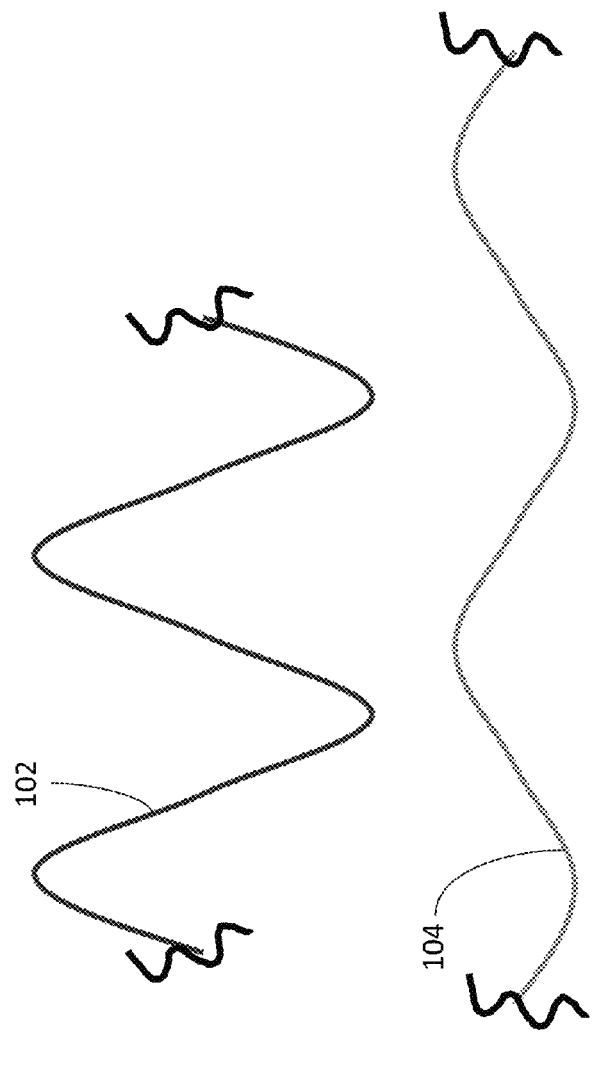
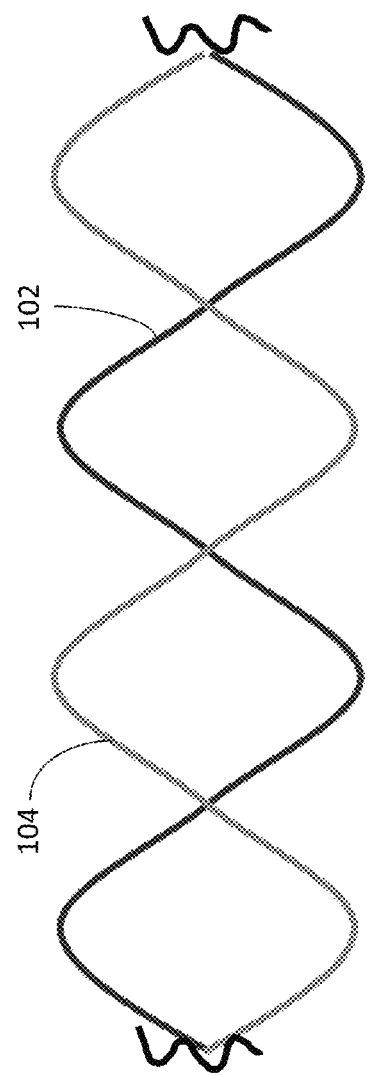

NON-WOVEN HELICAL WIRE STENT

RELATED APPLICATION

This application claims the benefit of priority from U.S. Provisional Application No. 61/515,081, filed Aug. 4, 2011, and titled "Non-Woven Helical Stent", the contents of which is incorporated herein by reference.

TECHNICAL FIELD

The present invention relates to medical devices and more specifically, stents.

BACKGROUND

Stents are tubular shaped medical devices commonly used to maintain patency of diseased body vessels. Stents may be implanted to treat blockages, occlusions, narrowing ailments, and other problems that can restrict flow through a vessel. Stents can be implanted, for example, in the coronary and peripheral arteries to maintain blood flow, in the ureters and biliary tract to provide drainage, and in the esophagus to palliate dysphagia.

Stents are often delivered in a radially compressed state via a minimally invasive procedure and thereafter expanded to contact and support the inner wall of the targeted vessel. Both self-expanding and balloon-expandable stents are amenable to radial compression and subsequent expansion at the treatment site. Balloon-expandable stents expand in response to the inflation of a balloon, whereas self-expanding stents deploy automatically when released from a delivery device.

Self-expanding stents are useful for a variety of procedures requiring the patency of a bodily pathway. Such stents are generally biased to expand, such that when deployed, they assume an open position, pushing outward and into the surrounding area into which deployed. The radial expansion creates a pathway in a once occluded area.

One type of self-expanding stent includes single wire stents designed for implantation in the gastrointestinal system (e.g., esphophagus, colon, biliary tree, etc). These braided stent structures are flexible enough to accommodate typical movements of such bodily organs, but they simultaneously provide sufficient rigidity to maintain patency of the vessel. A single wire stent typically includes a helical weave or braid configuration where the wires of opposing helicals pass in an alternating fashion under and over each other. This interweaved pattern gives stability to the stent structure. The current manufacturing process for these types of single wire woven stents is extremely labor intensive and expensive, as they are typically hand woven with the assistance of a mandrel. For larger stents, it can take up to sixteen hours for a highly skilled artisan to manufacture the tubular frame utilizing a wire measuring about eight meters in length. This long wire is laboriously threaded together to form the final stent weave pattern. Automated machine processes are currently unavailable.

Accordingly, what is needed is a stent and method of fabrication thereof that allows for efficient manufacture but maintains the described advantages of single wire woven stent structures.

BRIEF SUMMARY

In a first aspect, a stent is provided having a first wire configured into a first longitudinal tube having a proximal portion and a distal portion, and a lumen extending between the proximal portion and the distal portion, wherein the first longitudinal tube is configured to expand; and a second wire configured into a second longitudinal tube having a proximal portion and a distal portion, and a lumen extending between the proximal portion and the distal portion, wherein the second longitudinal tube is biased on compress;

wherein the second longitudinal tube is disposed about at least a portion of the first longitudinal tube in a non-woven manner.

In a second aspect, a method of manufacturing a stent is provided, the method including providing a first wire and a second wire; shape setting the first wire into a helical pattern biased to assume an expanded orientation; shape setting the second wire into a helical pattern biased to assume a compressed orientation; pulling longitudinally the first wire over a stent mandrel; fixing the first wire into place over the stent mandrel; compressing the second the second wire longitudinally; placing the second wire over the first wire on the stent mandrel forming a non-woven stent; and removing the stent from the stent mandrel.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

FIG. 1A illustrates a side view of shape set wires comprising the exemplary non-woven helical stent illustrated in FIG. 1;

FIG. 1B illustrates a side view of shape set wires comprising the exemplary non-woven helical stent illustrated in FIG. 1;

DETAILED DESCRIPTION OF PRESENTLY PREFERRED EMBODIMENTS

Figure 1:
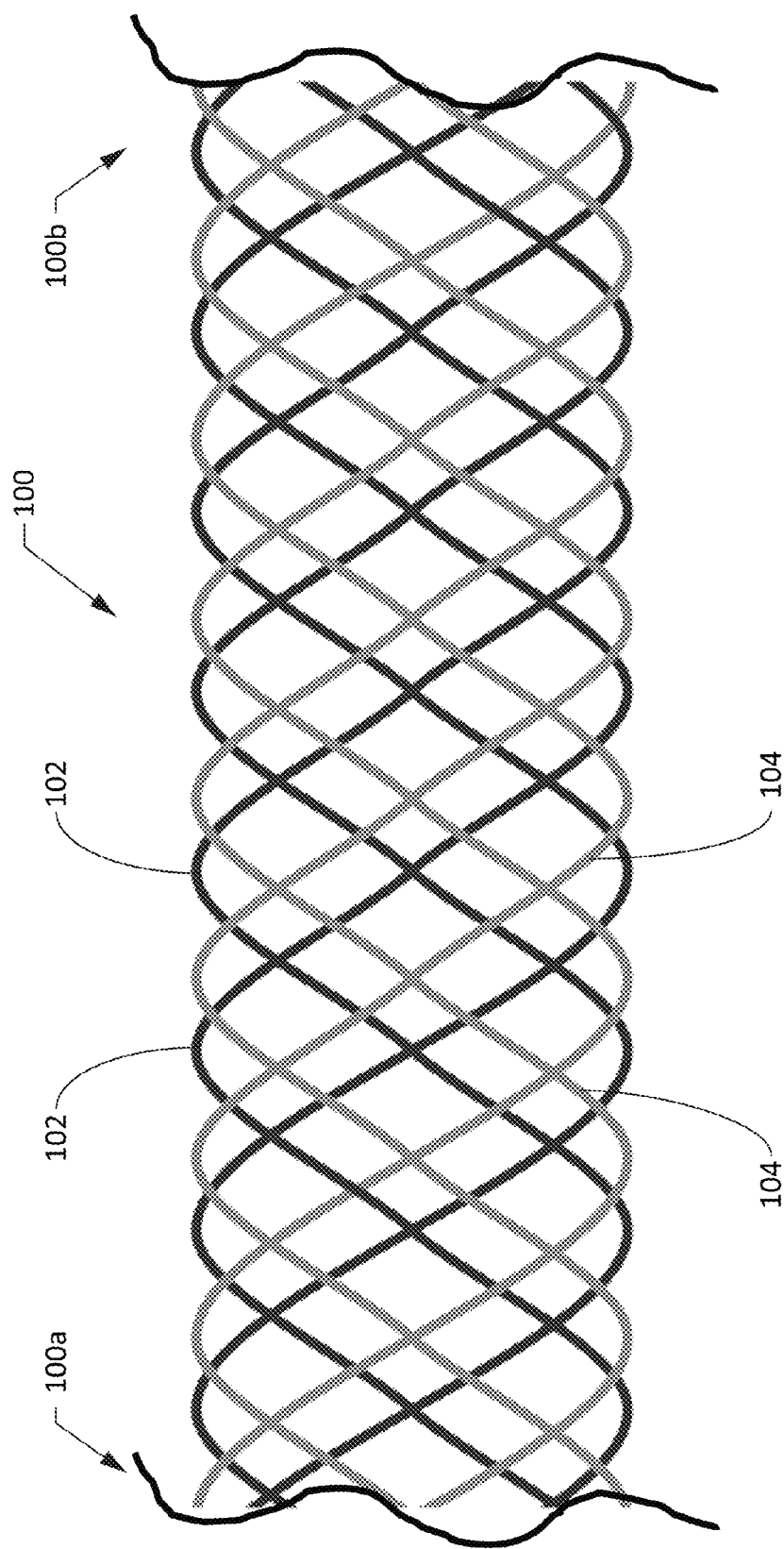
FIG. 1 illustrates a side view of an exemplary non-woven helical stent.

The exemplary embodiments illustrated herein provide the discovery of exemplary apparatuses and methods for stents that are not laborious to fabricate and that may be fabricated quickly, efficiently, and at decreased cost using a machine. The present invention is not limited to those embodiments described herein, but rather, the disclosure includes all equivalents including those of different shapes, sizes, and configurations, including but not limited to, other types of stents. For example, the principles herein can be applied to other types of stents, including but not limited to, self-expanding metal stents, self-expanding laser cut peripheral artery stents, laser cut self-expanding stents, woven wire stents, and the EVOLUTION® (Wilson-Cook Medical Inc.). The devices and methods can be used in any field benefiting from a stent, including but not limited to, the biliary, colonic, and esophageal regions. Additionally, the devices and methods are not limited to being used with a human being, others are contemplated, including but not limited to, animals.

A more detailed description of the embodiments will now be given with reference to FIGS. 1-5. Throughout the disclosure, like reference numerals and letters refer to like elements. The present disclosure is not limited to the embodiments illustrated; to the contrary, the present disclosure specifically contemplates other embodiments not illustrated but intended to be included in the claims.

FIG. 1 illustrates a side view of exemplary non-woven helical stent 100 having proximal portion 100a, distal portion 100b, first wire 102 and second wire 104. First wire 102 and second wire 104 are not woven or braided together as with traditional wire stents. Rather, first wire 102 and second wire 104 are each configured into a helical pattern, and second wire 104 is placed over first wire 102, wherein each of first wire 102 and second wire 104 are mechanically biased to force wires 102, 104 together and lend mechanical stability to the construction.

More specifically, referring to FIGS. 1A and 1B, wherein FIG. 1A illustrates a side view of shape set helical first wire 102 and shape set helical second wire 104 disconnected from each other, and FIG. 1B illustrates first wire 102 and second wire 104 in communication with each other and comprising exemplary non-woven helical stent 100 illustrated in FIG. 1.

Now referring to FIGS. 1, 1A, and 1B, first wire 102 is shape set such that it is biased to assume an expanded configuration, and second wire 104 is shape set such that it is biased to assume a compressed configuration. Thus, the construction of stent 100 is held together with the outwardly directed forces of first wire 102 and the inwardly directed forces of the second wire 104 cancelling each other out. This also causes frictions at the point where wires 102, 104 overlap to hold the construction together lending mechanical stability to the construction. The resulting construction, one embodiment of which is stent 100 illustrated in FIG. 1, has each helically configured wires 102, 104 wrapped to comprise multiple individual strands forming stent 100, wherein each of wires 102, 104 comprises a helical longitudinal tube which together form a helical mesh longitudinal tube.

The filaments or wires 102, 104 may be of various cross-sectional shapes and sizes. For example, wires 102, 104 may be flat in shape or may have a circular-shaped cross-section. Wires 102, 104 may have any suitable diameter, such as for example, from about 0.10 to about 0.30 mm.

As will be described in greater detail below, expandable stents illustrated and equivalents thereto may be formed from a variety of biocompatible materials. For example, wires 102, 104 preferably comprise one or more elastically deformable materials such as shape memory alloys (e.g., stainless steel, nitinol, and the like), although other materials are contemplated. For example, wires 102, 104 may also be made from or comprise any suitable biocompatible material(s). For example, stents illustrated and equivalents thereto may include materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and or composites or alloys. Examples of other materials that may be used in part to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

Stents illustrated and equivalents thereto may be fabricated to any suitable dimensions. Stents illustrated and equivalents thereto having a particular length and diameter may be selected based on the targeted vessel. For example, a stent designed for esophageal implantation may have a length ranging from about 5 cm to about 15 cm and a body diameter of about 15 mm to about 25 mm. Optionally, an esophageal stent may include one or more flanges or flares of about 10 mm to about 25 mm in length and about 20 mm to about 30 mm in diameter. A stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

Stents illustrated and equivalents thereto may be delivered to a body lumen using various techniques. Generally, under the aid of endoscopic and/or fluoroscopic visualization a delivery device containing the stent is advanced into the vicinity of the target anatomy. The targeted lumen may be predilated with a balloon catheter or other dilation device, if necessary or desired. Preferably, the stent is delivered in a compressed state in a low profile delivery device. This approach may reduce the risk of tissue perforations during delivery. Once the delivery device is in place, the stent may be released from the retaining sheath or the like. In one preferred embodiment, a stent may be delivered with a controlled release system (e.g., EVOLUTION® Controlled-Release Stent, Cook Endoscopy Inc., Winston-Salem, N.C.). A controlled release device permits the physician to slowly release the stent from the retaining sheath and in some instances, recapture the stent to allow for repositioning. After implantation, the delivery device and any other devices (e.g., wire guides, catheters, etc.) may be removed.

It is also contemplated that stents illustrated and equivalents thereto are capable of being delivered and placed with the system described in U.S. patent application Ser. No. 13/015,764, entitled "Mechanically Expandable Delivery and Dilation Systems," filed Jan. 28, 2011, and incorporated in its entirety herein by reference, describing, for example, a stent delivery system that includes an elongate shaft including a proximal portion, a distal portion, a lumen extending at least partially therethrough, and a stent receiving portion on the distal portion of the shaft. The stent delivery system also includes a stent positioned at the stent receiving portion of the elongate shaft, the stent having a constrained configuration and an expanded configuration, a proximal constraining member and a distal constraining member releasably connected to the stent and having a first position and a second position are also included, wherein the proximal constraining member and the distal constraining member cooperatively apply a longitudinal tensile force to at least a portion of the stent in the constrained configuration with the proximal and distal constraining members each in the first position.

Stents illustrated and equivalents thereto may have any suitable helical pattern or angle such as those illustrated in FIGS. 1, 2-3, as further discussed below. The radial force of the stent may be controlled by adjusting the angle accordingly. Stents with higher angles typically exert greater radial force and exhibit greater foreshortening during expansion from a compressed state. Stents with lower angles typically exert lower radial force and experience less foreshortening upon expansion. In some instances, the angle can be lowered because the membrane covering typically adds rigidity to the stent structure. Coverings contemplated are further discussed in conjunction with FIG. 2. In addition to adjusting the angle, the radial force of the stent can be adjusted through selection of particular filament materials, as well as the shape and size of the filaments or wires forming the stent structure.

Stents illustrated and equivalents thereto may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of wires 102, 104. In some embodiments, a stent may include four radiopaque markers with two markers affixed to a first flange and two to a second flange. Optionally, radiopacity can be added to a stent through covering (also referred to as coating) processes such as sputtering, plating, or co-drawing gold or similar heavy metals onto the stent. Radiopacity can also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate.

Stents illustrated and equivalents thereto may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents may be preferred for use in vessels that are subject to changes in shape and/or changes in position, such as those of the peripheral and gastrointestinal systems. Peripheral vessels regularly change shape as the vessels experience trauma from external sources (e.g., impacts to arms, legs, etc.); and many gastrointestinal vessels naturally change shape as peristaltic motion advances food through the digestive tract. One common procedure for implanting a self-expanding stent involves a two-step process. First, if necessary, the diseased vessel may be dilated with a balloon or other device. The stent may be loaded within a sheath that retains the stent in a compressed state for delivery to the targeted vessel. The stent may then be guided to the target anatomy via a delivery catheter and thereafter released by retracting or removing the retaining sheath. Once released from the sheath, the stent may radially expand until it contacts and presses against the vessel wall. In some procedures, self-expanding stents may be delivered with the assistance of an endoscope and/or a fluoroscope. An endoscope provides visualization as well as working channels through which devices and instruments may be delivered to the site of implantation. A fluoroscope also provides visualization of the patient anatomy to aid in placement of an implantable device, particularly in the gastrointestinal system.

Mechanically expandable stents (e.g., balloon expandable stents) may be made from plastically deformable materials (e.g., 316L stainless steel). A balloon-expandable stent may be crimped and delivered in a reduced diameter and thereafter expanded to a precise expanded diameter. Balloon expandable stents can be used to treat stenosed coronary arteries, among other vessels. One common procedure for implanting a balloon expandable stent involves mounting the stent circumferentially on a balloon-tipped catheter and threading the catheter through a vessel passageway to the target area. Once the balloon is positioned at the targeted area, the balloon may be inflated to dilate the vessel and radially expand the stent. The balloon may then be deflated and removed from the passageway.

Figure 2:
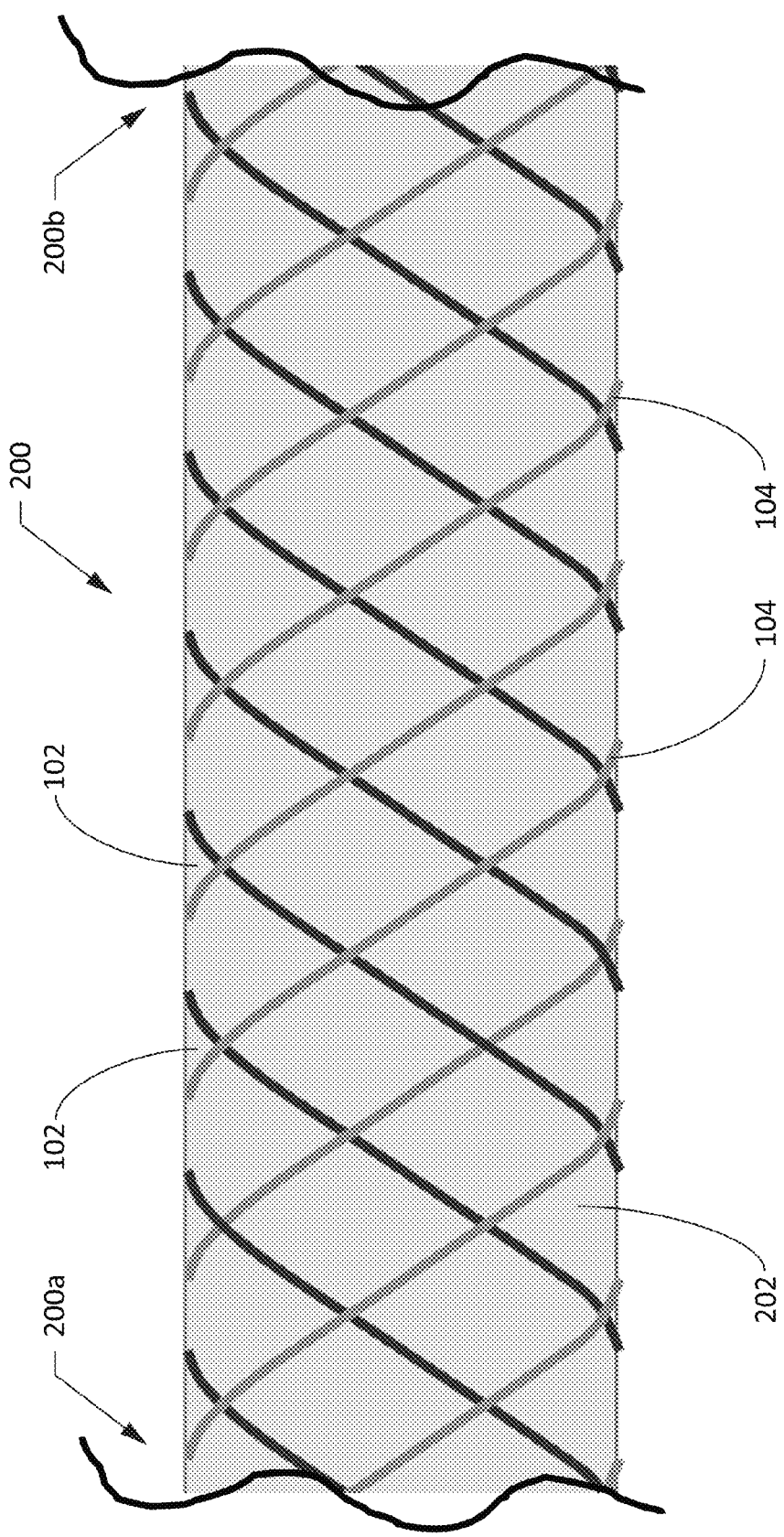
FIG. 2 illustrates an alternate embodiment of an exemplary non-woven helical stent.

FIG. 2 illustrates an alternate embodiment of exemplary non-woven helical stent 200 having proximal portion 200a and distal portion 200b, and it is similar to stent 100 illustrated in FIG. 1. Stent 200 is covered in a silicone covering 202 that is integrated with wires 102, 104 and prevents tissue in-growth. Covering 202 may be adapted to prevent or limit the motion between wires 102, 104 at crossover points for stent 200 to better function and flex. It is also contemplated that holes could be provided in covering 202 for uses where drainage would be desired, including but not limited to, usage in the biliary region where side branch drainage may be desired.

Although covering 202 is illustrated as being a silicone elastomer, which is desired given its ability to stretch generally 500-700% without being compromised and such, is useful in stent applications, other covering materials are contemplated, including but not limited to, polyethane (the fibers of which could be applied in layers at the same pitch of wires 102, 104 to help close the gaps and provide a seal-like covering (but an air or water-tight seal need not be achieved)), TYVEK® (DuPont) (or other like materials) which are contemplated as being sandwiched between first wire 102 and second wire 104, as well as other non-woven materials. Indeed it is also completed that other fabric layers with filaments running in one direction that matches the pitch of one or more of stent wires 102, 104 could be used as a covering. As such, the covering could be made up of several layers with the filaments running in one direction with a pitch similar to one or more of wires 102, 104 of stent 200 with the direction of the helical pattern alternated between layers. It is contemplated that such fabric layer may be bonded to one or more of wires 102, 104 of stent 200.

Indeed, in some embodiments, the covering membrane may cover over the entire stent framework from the proximal end to the distal end. In other embodiments, the stent may have a covering over a central portion of the structure and one or more uncovered ends or flanges. Moreover, a membrane covering may comprise any suitable biocompatible material. Preferably, the membrane covering is an elastic or flexible material that can adapt to radial compression of a stent prior to delivery, as well as foreshortening of a stent during expansion from a compressed state. Suitable membrane materials include, for example, as discussed above, silicones (e.g. polysiloxanes and substituted polysiloxanes), polyurethanes, thermoplastic elastomers, polyolefin elastomers, polyethylene, polytetrafluoroethylene, nylon, and combinations thereof. In some embodiments, where the stent will be implanted at or near an acidic environment (e.g., being exposed to gastric fluids), preferably the membrane covering is resistant to acid degradation.

Stents illustrated and equivalents thereto may include a membrane covering applied by any suitable method as is known in the art. For example, the membrane may be applied by spraying, dipping, painting, brushing, or padding. Generally, the membrane covering has a thickness ranging from about 0.0025 mm to about 2.5 mm. The thickness of the membrane may be selected, for example, by controlling the number of dips or passes made during the application process.

In some embodiments, a stent may include one or more bioactive agents coated on the stent surfaces. A bioactive agent may be applied directly on the surface of the stent (or on a primer layer which is placed directly on the surface of the stent). Alternatively, the bioactive agent may be mixed with a carrier material and this mixture applied to the stent. In such configuration, the release of the bioactive agent may be dependent on factors including composition, structure and thickness of the carrier material. The carrier material may contain pre-existing channels, through which the bioactive agent may diffuse, or channels created by the release of bioactive agent, or another soluble substance, from the carrier material.

One or more barrier layers may be deposited over the layer containing the bioactive agent. A combination of one or more layers of bioactive agent, mixtures of carrier material/bioactive, and barrier layers may be present. The bioactive agent may be mixed with a carrier material and coated onto the stent and then over coated with barrier layer(s). Multiple layers of bioactive agent, or mixtures of carrier material/bioactive, separated by barrier layers may be present to form a stent having multiple coverings. Different bioactive agents may be present in the different layers.

The carrier material and/or the barrier layer can include a bioelastomer, PLGA, PLA, PEG, Zein, or a hydrogel. In some other embodiments, the carrier material and/or the barrier layer includes microcrystalline cellulose, hydroxypropylmethyl cellulose, hydroxypropyl cellulose, a cellulose product, a cellulose derivative, a polysaccharide or a polysaccharide derivative. The carrier material and/or barrier layer may include lactose, dextrose, mannitol, a derivative of lactose, dextrose, mannitol, starch or a starch derivative. The carrier material and/or barrier layer may include a biostable or a biodegradable material, for example, a biostable or biodegradable polymer.

A variety of bioactive agents may be applied to the stent in accordance with the intended use. For example, bioactive agents that may be applied include antiproliferative/antimitotic agents including natural products such as vinca alkaloids (vinblastine, vincristine, and vinorelbine), paclitaxel, rapamycin analogs, epidipodophyllotoxins (etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (for example, L-asparaginase which systemically metabolizes L-asparagine and deprives cells which do not have the capacity to synthesize their own asparagine); antiplatelet agents such as (GP) II b/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat.

A bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition or any other method known.

Prior to applying a membrane covering, and/or a bioactive agent, a stent may be polished, cleaned, and/or primed as is known in the art. A stent may be polished, for example, with an abrasive or by electropolishing. A stent may be cleaned by inserting the stent into various solvents, degreasers and cleansers to remove any debris, residues, or unwanted materials from the stent surfaces. Optionally, a primer coating may be applied to the stent prior to application of a membrane covering, bioactive, or other coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure. A primer layer may comprise, for example, silane, acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

In addition the use of a covering, prevention or the limiting of motion between wires 102, 104 could also be achieved or aided by placing a bump feature onto one or more of wires 102, 104 at the places where wires 102, 104 cross each other, such as by roughening the surface of wires 102, 104 (or one of wires 102, 104 or portions thereof) at the cross-over points such as where second wire 104 crosses over first wire 102 to help wires 102, 104 engage each other and prevent wire migration by way of increased friction between wires 102, 104. Roughening of the surface of one or more of wires 102, 104 or portions thereof can be achieved by means of, including but not limited to, filing and sand blasting. A weld may also be placed at one or more cross over points as a securing means.

Figure 3:
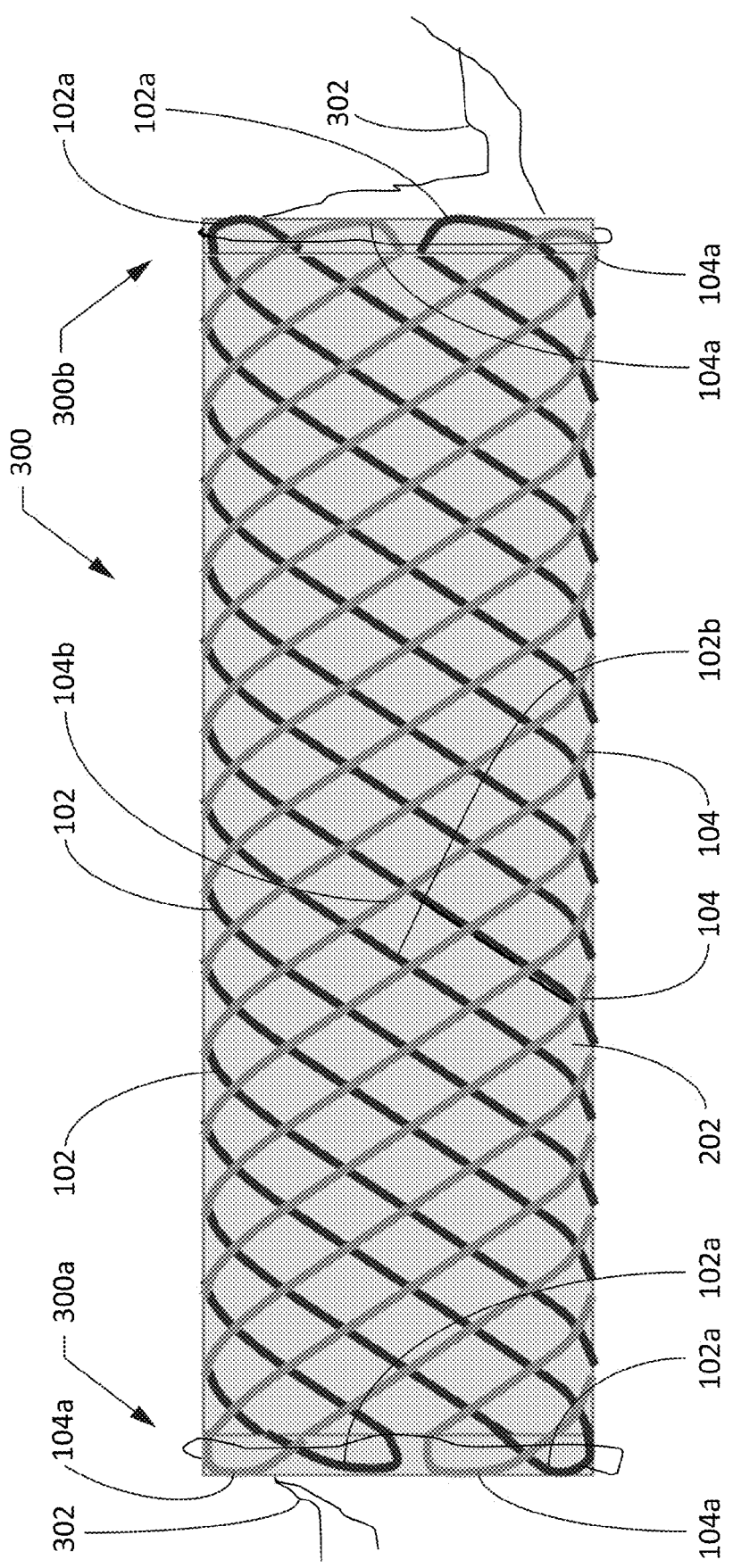
FIG. 3 illustrates an alternate embodiment of an exemplary non-woven helical stent.

FIG. 3 illustrates an alternate embodiment of exemplary non-woven helical stent 300 having proximal portion 300a and distal portion 300b, and it is similar to stents 100 and 200 illustrated in FIGS. 1 and 2. Stent 300 has wires 102, 104 each of which are wound back to form crowns such that crowns 102a are formed from first wire 102, and crowns 104a are formed from second wire 104. It is contemplated that first wire crowns 102a and second wire crowns 104a may overlap. Indeed, it is contemplated that a securing means, including but not limited to, a band or weld could be made between wires 102, 104 to hold crowns 102a, 104a or portions thereof in place thereby altering the mechanical properties of stent 300 and improving stability. Ends 102b, 104b, of wires 102, 104 are preferably run parallel to each other and held in place, for example, by a securing means, including but not limited to, covering 202. Alternatively, a weld or other securing means or combination thereof may be utilized.

Attached at proximal portion 300a and distal portion 300b are purse strings 302, such as a loop, lasso, or suture. A stent may include one or more purse strings, such as loops, lassos, or sutures on the stent structure to facilitate repositioning or removal of the stent during or after implantation. For example, a stent may include a loop at or near the proximal end and/or distal end of the stent. The loop material may circumscribe the end and in some embodiments may be wound through the absolute end cells to affix the loop to the stent. The loop may comprise any appropriate biocompatible materials, such as for example, suture materials or other polymeric or metallic materials such as polyethylene, ultra-high molecular weight polyethylene, polyester, nylon, stainless steel, nitinol, or the like. Optionally, the lasso may be covered with a material, such as polytetrafluoroethylene, to reduce frictional interactions of the lasso with surrounding tissue. The purse string may be configured to compress the stent when an axial force is applied to it.

Although the aforementioned illustrated embodiments depict a stent having a substantially uniform diameter on the longitudinal axis, other stent configurations are possible.

Figure 4:
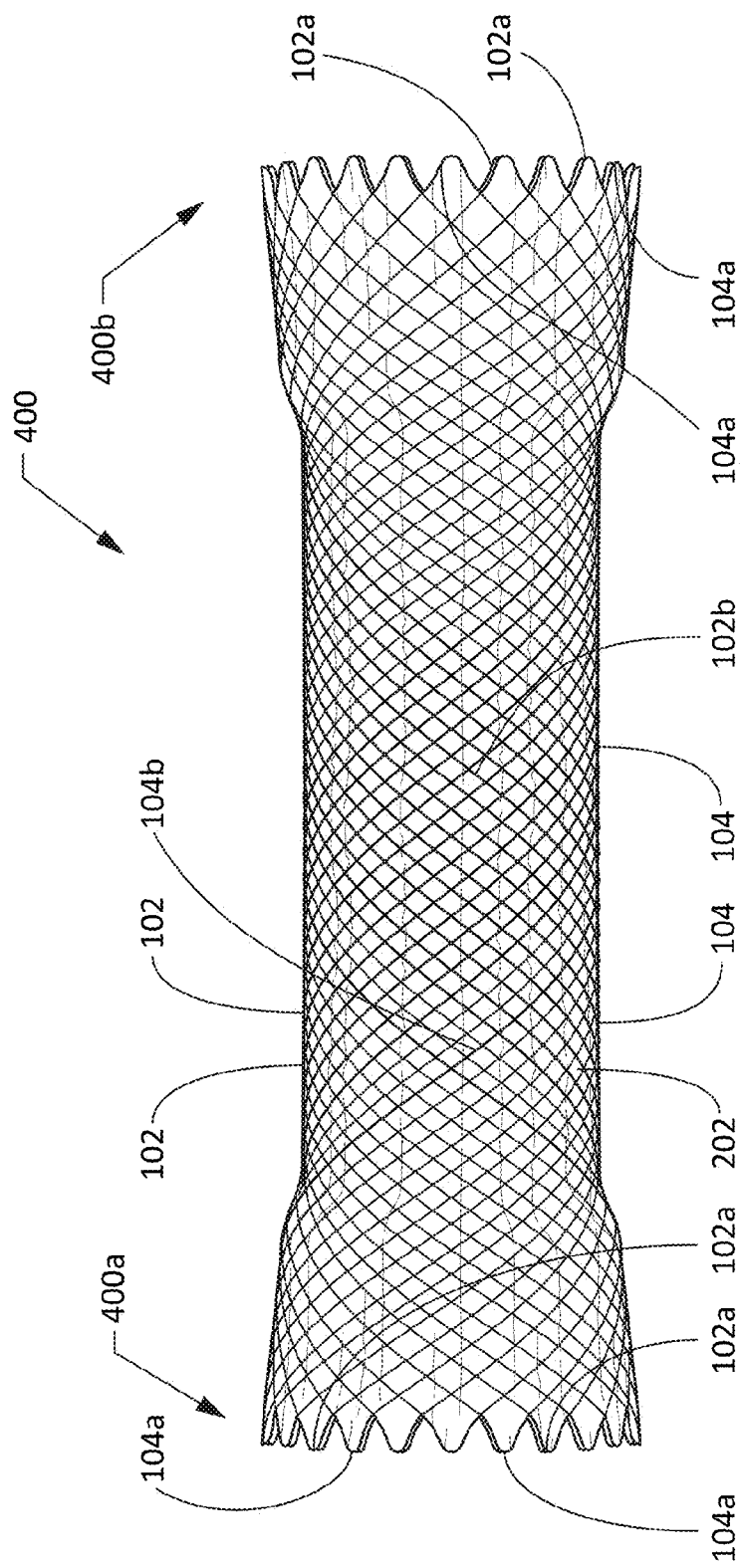
FIG. 4 illustrates an alternate embodiment of an exemplary non-woven helical stent having flared ends.

Now referring to FIG. 4 which illustrates an alternate embodiment of exemplary non-woven helical stent 400, which is similar to stents 100, 200, and 300 illustrated in FIGS. 1, 2, and 3. A stent may include a central body portion and one or more uniform flanges, or it may have two asymmetrically shaped flanges. A stent may include a uniform diameter along the length of stent 400 but include slightly flared proximal end 400a and/or distal end 404b of stent 400. The central body portion may smoothly transition to a flange or flare, or alternatively, may progressively step up in diameter to a flange or flare. Generally, a stent may be implanted in a vessel (e.g., esophagus, duodenum, colon, trachea, or the like) such that the central body portion engages a diseased area and the proximal and distal ends engage healthy tissue adjacent the diseased area.

Additionally, wires 102, 104 may be wound such that the pitch is changed providing for greater mechanical stability. For example, first wire 102 is first wound in a clockwise fashion forming a first layer of stent 400, and it is turned to form a portion of crowns 102a. First wire 102 is then wound in an orientation that is generally opposite the first layer, such as in a counterclockwise fashion over the first layer of stent 400 to form the second layer of stent 400. First wire 102 is then turned to form a portion of crowns 102a, and it is subsequently wound in a clockwise fashion forming a third length of stent 400 over the second layer. Second wire 104 is then wound in a counterclockwise fashion over the third layer of stent 400 forming the fourth layer of stent 400, and it is then turned to form a portion of crowns 104a. Second wire 104 is then wound in a clockwise fashion to form a fifth layer of stent 400 over the fourth layer of stent 400. Second wire 104 is then turned to form a portion of crowns 104a, and it is then wound in a counterclockwise fashion to form a sixth layer of stent 400 over the fifth layer of stent 400. Ends 102b, 104b, of wires 102, 104 are preferably run parallel to each other and held in place, for example, by a securing means, including but not limited to, covering 202. Alternatively, a weld or other securing means or combination thereof may be utilized.

Figure 5:
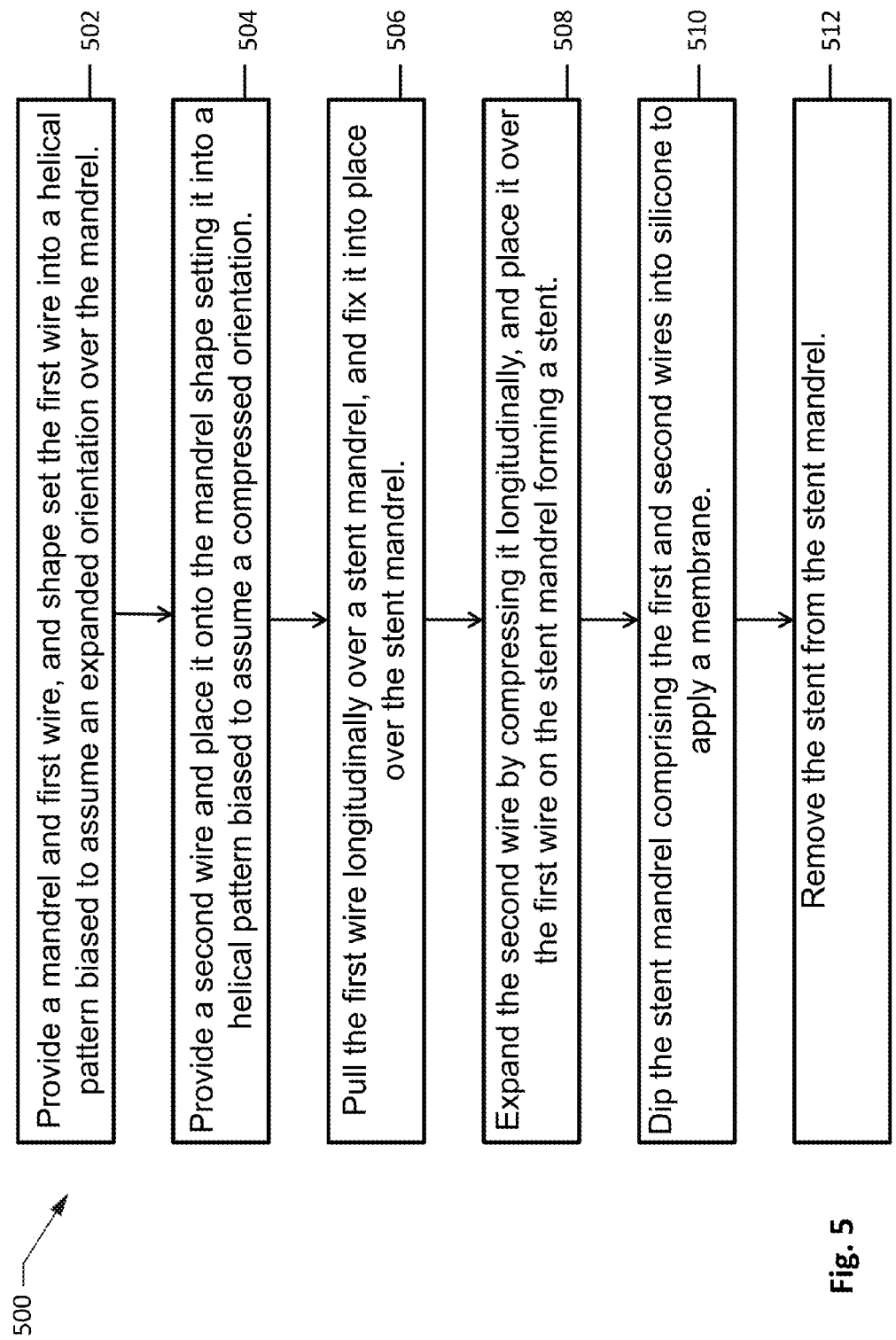
FIG. 5 illustrates an exemplary method of manufacturing a non-woven helical stent.

FIG. 5 illustrates an exemplary method of manufacturing a non-woven helical stent 500, including but not limited to, those illustrated in FIGS. 1-4.

At block 502, a mandrel and first wire are provided, and the first wire is shape set into a helical pattern biased to assume an expanded orientation over the mandrel.

At block 504, a second wire is provided and placed onto the mandrel, and the second wire is shape set into a helical pattern biased to assume a compressed orientation;

At block 506, the first wire is pulled longitudinally over a stent mandrel and fixed into place over the stent mandrel.

At block 508, the second wire is expanded by compressing it longitudinally and placed over the first wire on the stent mandrel forming a stent.

At block 510, optionally, the stent mandrel comprising the first and second wires is dipped into a silicone (or other covering), to apply a membrane.

At block 512, the stent is removed from the stent mandrel.

Ends of wires are preferably run parallel to each other and held in place, for example, by a securing means, including but not limited to, a covering. Alternatively, a weld or other securing means may be utilized. Optionally a purse string, such as that illustrated in FIG. 3, can be attached to the stent. Additionally, the principles illustrated, including but not limited to, those illustrated and discussed in conjunction with FIGS. 1-4, can be applied, including but not limited to, flaring a proximal and/or a distal portion of the stent.

From the foregoing, the discovery of a non-woven helical stent that is efficient to fabricate by being able to be manufactured by hand or machine while providing mechanical stability equivalent or close thereto of known braided or woven stents will benefit patients both in having an improved means for treating ailments as well as likely reducing the cost of treatment. It can be seen that the stents illustrated and equivalents thereof as well as the methods of manufacturer may utilize machines or other resources, such as human beings, thereby reducing the time, labor, and resources required to manufacturer a stent. Indeed, the discovery is not limited to the embodiments illustrated herein, and the principles and methods illustrated herein can be applied and configured to any stent and equivalents.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages described above are not necessarily the only advantages of the discovery, and it is not necessarily expected that all of the described advantages will be achieved with every embodiment of the discovery.

What is claimed is:

1. A stent comprising:
a first wire configured into a non-woven first longitudinal tube having a first helical pattern and comprising a proximal portion and a distal portion, and a lumen extending between the proximal portion and the distal portion, wherein the first longitudinal tube is outwardly biased to assume an expanded configuration; and
a second wire configured into a non-woven second longitudinal tube having a second helical pattern and comprising a proximal portion and a distal portion, and a lumen extending between the proximal portion and the distal portion, wherein the second longitudinal tube is inwardly biased to assume a compressed configuration;
wherein the first helical pattern of the first longitudinal tube is opposite to the second helical pattern of the second longitudinal tube;
wherein the second longitudinal tube is disposed about at least a portion of the first longitudinal tube in a non-woven manner; and
wherein the outwardly bias of the first longitudinal tube and the inwardly bias of the second longitudinal tube combine to form a mechanically stable assembled stent that is expandable from a compressed delivery configuration to an expanded deployed configuration.

2. The stent of claim 1, further comprising a covering affixed to at least a portion of one of the first longitudinal tube or the second longitudinal tube.

3. The stent of claim 2, wherein the covering comprises silicone.

4. The stent of claim 1, further comprising a covering disposed between at least a portion of the first longitudinal tube and the second longitudinal tube.

5. The stent of claim 1, wherein at least one of the first wire or the second wire comprises a shape-memory alloy.

6. The stent of claim 1, wherein at least one of the first wire or the second wire comprises nitinol.

7. The stent of claim 1, wherein the first wire of the first longitudinal tube comprises a first non-woven layer wound in a clockwise helical orientation; and wherein the second wire of the second longitudinal tube comprises a second non-woven layer wound in a counterclockwise helical orientation.

8. The stent of claim 1, wherein the second wire of the second longitudinal tube comprises a second non-woven layer wound in a clockwise helical orientation; and wherein the first wire of the first longitudinal tube comprises a first non-woven wire wound in a counterclockwise helical orientation.

9. The stent of claim 1, wherein the first wire comprises a first and second end and the second wire comprises a first and second end; wherein at least one of the first or second end of the first or second wire is secured by a weld.

10. The stent of claim 1, wherein the first wire comprises a first and second end and the second wire comprises a first and second end; wherein at least one of the first or second end of the first or second wire is secured by a covering.

11. The stent of claim 1, wherein the first wire comprises a first and second end and the second wire comprises a first and second end; wherein at least one of the first or second end of the first or second wire is secured by a securing means.

12. The stent of claim 1, wherein the stent further comprises a proximal portion and a distal portion, wherein at least one of the proximal portion or the distal portion comprises a purse string attached thereto and configured to compress the stent.

13. The stent of claim 1, wherein the stent further comprises a proximal portion and a distal portion, wherein at least one of the proximal portion or the distal portion is configured into a flared orientation.

14. The stent of claim 1, wherein the first longitudinal tube comprises an overall length that is about equal to an overall length of the second longitudinal tube, and wherein the second longitudinal tube is disposed about the first longitudinal tube in a fully overlapping configuration.

15. The stent of claim 1, wherein the first wire of the first longitudinal tube is separate from the second wire of the second longitudinal tube.

16. The stent of claim 1, wherein the assembled stent is self-expandable from the compressed delivery configuration to the expanded deployed configuration.

17. The stent of claim 1, wherein the assembled stent is mechanically expandable from the compressed delivery configuration to the expanded deployed configuration.

18. A non-woven stent comprising:
a first wire configured into a first non-woven longitudinal tube comprising a proximal portion and a distal portion, and a lumen extending between the proximal portion and the distal portion, wherein the first non-woven longitudinal tube is outwardly biased to assume an expanded configuration; and
a second wire configured into a second non-woven longitudinal tube comprising a proximal portion and a distal portion, and a lumen extending between the proximal portion and the distal portion, wherein the second non-woven longitudinal tube is inwardly biased to assume a compressed configuration;
wherein the first non-woven longitudinal tube and the second non-woven longitudinal tube each comprise a helical pattern, the helical pattern of the first non-woven longitudinal tube having a helical orientation opposite that of the helical pattern of the second non-woven longitudinal tube;
wherein the second non-woven longitudinal tube is disposed about at least a portion of the first non-woven longitudinal tube in a non-woven manner;
wherein the outwardly bias of the first non-woven longitudinal tube and the inwardly bias of the second non-woven longitudinal tube combine to form a mechanically stable assembled stent that is expandable from a compressed delivery configuration to an expanded deployed configuration; and
wherein the stent further comprises a proximal portion and a distal portion, wherein at least one of the proximal portion or the distal portion comprises a purse string attached thereto and configured to compress the stent.

* * * * *